(12) United States Patent
Niederberger

(10) Patent No.: US 9,022,954 B2
(45) Date of Patent: May 5, 2015

(54) DEVICE FOR MEASURING REAL-TIME PRESSURE EXERTED BY A SUPPORT SURFACE ON A PERINEAL ARTERY

(75) Inventor: Craig S. Niederberger, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1332 days.

(21) Appl. No.: 12/778,241

(22) Filed: May 12, 2010

(65) Prior Publication Data

US 2010/0292615 A1 Nov. 18, 2010

Related U.S. Application Data

(60) Provisional application No. 61/177,583, filed on May 12, 2009.

(51) Int. Cl.
| | |
|---|---|
| *A61B 5/02* | (2006.01) |
| *A61B 5/117* | (2006.01) |
| *A61B 5/103* | (2006.01) |
| *A61B 5/00* | (2006.01) |

(52) U.S. Cl.
CPC .............. *A61B 5/103* (2013.01); *A61B 5/4393* (2013.01); *A61B 5/6813* (2013.01); *A61B 5/7275* (2013.01)

(58) Field of Classification Search
CPC ..................................................... A61B 5/103
USPC .......................... 600/587, 561, 595, 591, 490
See application file for complete search history.

(56) References Cited

U.S. PATENT DOCUMENTS

| | | | |
|---|---|---|---|
| 4,414,984 | A | 11/1983 | Zarudiansky |
| 6,019,423 | A | 2/2000 | Dodge et al. |
| 6,272,936 | B1 | 8/2001 | Oreper et al. |
| 6,302,840 | B1 | 10/2001 | Benderev |
| 6,743,165 | B2 | 6/2004 | Mosel et al. |
| 6,807,869 | B2 | 10/2004 | Farringdon et al. |

(Continued)

FOREIGN PATENT DOCUMENTS

| | | |
|---|---|---|
| JP | 10248890 A * | 9/1998 |
| WO | WO2011/143316 | 11/2011 |

OTHER PUBLICATIONS

Minkow. "Body Geometry Story" www.specialized.com/OA_MEDIA/whatsnew/BGWhitePages.pdf, Mar. 2006.*

(Continued)

*Primary Examiner* — Brian Szmal
(74) *Attorney, Agent, or Firm* — Michael Best & Friedrich LLP

(57) ABSTRACT

Provided are methods and devices for measuring real-time pressures on the perineum of a user positioned on a surface. In an embodiment the surface is a bicycle seat and the real-time measurement is a pressure map of the pressure distribution during a bicycle ride. The methods relate to connecting a pressure sensor to the perineum region of the user, positioning the user on the surface, wherein the pressure sensor is positioned between the perineum and the surface, and obtaining output from the pressure sensor while the user is positioned on the surface, such as during a bicycle ride. The devices relate to a plurality of pressure sensors capable of being connected to the perineum region and a microcontroller containing a drive circuit and chip for analog-to-digital conversion and storage. One use of the methods and devices are to assess risk of erectile dysfunction for bicycle riders.

20 Claims, 6 Drawing Sheets

(56) References Cited

U.S. PATENT DOCUMENTS

| | | | |
|---|---|---|---|
| 6,964,205 | B2 | 11/2005 | Papakostas et al. |
| 7,258,026 | B2 | 8/2007 | Papakostas et al. |
| 7,338,417 | B2* | 3/2008 | Kang ........................ 482/148 |
| 7,845,225 | B2 | 12/2010 | Ridenour et al. |
| 2003/0009181 | A1 | 1/2003 | Gellman |
| 2003/0107479 | A1* | 6/2003 | Evans ........................ 340/427 |
| 2004/0237666 | A1* | 12/2004 | Winkenbach et al. ..... 73/862.49 |
| 2007/0258674 | A1* | 11/2007 | Wang et al. .................... 385/13 |
| 2009/0058661 | A1 | 3/2009 | Gleckler et al. |
| 2010/0069784 | A1 | 3/2010 | Blaivas |

OTHER PUBLICATIONS

Sommers et al. "Erectile Dysfuncton in Cyclists", submitted by applicant.*

International Search Report and Written Opinion for PCT application PCT/US11/36083 Aug. 15, 2011—8 pages.

Benjamin, B.E. (2004) "Cycling and Your Health," *Massage Therapy J.*

Blakeslee, S. (Oct. 4, 2005) "Serious Riders, Your Bicycle Seat May Affect Your Love Life/Strong," *New York Times*.

Breda et al. (2005) "Development of a New Geometric Bicycle Saddle for the Maintenance of Genital-Perineal Vascular Perfusion," *J. Sex. Med.* 2:605-611.

Forghani et al. (May 2008) "Design and Fabrication of a Device Measuring Perineal Pressures Real-Time During Bicycle Riding to Determine Erectile Dysfunction Risk," Poster Presented at the 2008 Annual Meeting of the American Urological Association; May 17-22, Orlando Florida.

Forghani et al. (May 19, 2008) "Design and Fabrication of a Device Measuring Perineal Pressures Real-Time During Bicycle Riding to Determine Erectile Dysfunction Risk," *J. Urology* 179(4)Supplement:281 Abstract # 809.

Huang et al. (2005) "Bicycle Riding and Erectile Dysfunction: An Increase in Interest (and Concern)," *J. Sex. Med.* 2:596-604.

Lowe et al. (2004) "Effects of Bicycle Saddle Designs on the Pressure to the Perineum of the Bicyclist," *Med. Sci. Sports Exerc.* 36(6):1055-1062.

Munarriz et al. (2005) "Only the Nose Knows: Penile Hemodyamic Study of the Perineum-Saddle Interface in Men with Erectile Dysfunction Utilizing Bicycle Saddles and Seats with and Without Nose Extensions," *J. Sex. Med.* 2:612-619.

National Institute for Occupational Safety and Health Report (2009) "No-Nose Saddles for Preventing Genital Numbness and Sexual Dysfunction from Occupational Bicycling," *Niosh Pub.* No. 2009-131.

Novel "Pliance Saddle Systems," http://www.novel.de/old/nav2/nav_215.htm, Accessed Apr. 5, 2010.

Schrader et al. "Your Health and Bike Seats," Spongy Wonder Bicycle Seats, http://www.Spongywonder.com/Yourhealth.htm , Accessed Apr. 5, 2010.

Schrader et al. (2008) "Cutting Off the Nose to Save the Penis," *J. Sex. Med.* 5:1932-1940.

Schrader et al. (2002) "Nocturnal Penile Tuminescnece and Rigidity Testing in Bicycling Patrol Offices," *J. Andrology*23(6):927-934.

Sommer et al. (2001) "Erectile Dysfunction in Cyclists," *Eur. Urol.* 39(6):720-723.

Tekscan (Feb. 5, 2009) "FlexiForce® Sensors User Manual," http://www.tekscan.com/pdf/FlexiForce-Sensors-Manual.pdf.

\* cited by examiner

DEVICE FOR MEASURING REAL-TIME PRESSURE EXERTED BY A SUPPORT SURFACE ON A PERINEAL ARTERY

CROSS-REFERENCE TO RELATED APPLICATIONS

This application claims the benefit of U.S. Provisional Application No. 61/177,583, filed May 12, 2009, which is specifically incorporated by reference to the extent not inconsistent herewith.

BACKGROUND OF THE INVENTION

Provided herein are various devices and methods that measure real-time perineal pressures during bicycle riding. The devices and methods are particularly useful for design of bicycle seats for comfort and to minimize risk of erectile dysfunction (ED) for a rider. Furthermore, the devices and methods can be used as a tool to assess ED risk for a rider using a specific bicycle seat, wherein the rider uses the seat under real ride conditions.

An important component of bicycles is the bicycle seat. Much work has gone into developing bicycles seats that are comfortable and perform well under different conditions ranging from the recreational to the competitive user. There has been increasing recognition that bicycle riding can be a significant risk factor for ED (see, e.g., Ben E. Benjamin "Cycling and Your Health" Massage Therapy Journal. 2004). In particular, due to the positioning of the rider and seat geometry, it is not uncommon for riders to experience discomfort in the perineal region, particularly for longer-duration rides. In fact, genital numbness due to cycling is observed and riders report impaired sexual function and increase in ED. Accordingly, numerous studies have further investigated the relationship between bicycle riding and ED.

For example, Huang et al. ("Bicycle Riding and Erectile Dysfunction: An Increase in Interest (and Concern)" J. Sex. Med. 2005:596-604) summarizes various scientific publications in peer-reviewed journals from 1981 to 2004 and concludes that "bicycle riding more than 3 hours per week was an independent relative risk . . . for moderate to severe ED." The authors of that study hypothesize that "straddling bicycle saddles with a nose extension is associated with suprasystolic perineal compression pressures, temporarily occluding penile perfusion and potentially inducing endothelial injury and vasculogenic ED."

Such a conclusion is based, at least in part, on studies using stationary bikes with sensors on the saddle that suggest bicycling may cause ED. For example, Schrader et al. (2002) used a "thin profile resistance-based pressure measurement mat . . . placed over the saddle" to measure pressure exerted between the rider and the bicycle saddle. "Nocturnal Penile Tumescence and Rigidity Testing in Bicycling Patrol Offices" J. of Andrology (2002) 23(6): 927-934. Pressure distribution maps were illustrated for a man sitting on a chair and in different positions on a bicycle saddle (normal/upright or in pursuit position). The results of that study suggested "prolonged bicycle riding may have negative effects on nocturnal erectile function and indicate a need for innovative bicycle saddle designs." A similar follow-on study of bicycle police officers assessed the effectiveness of "no-nose bicycle saddle as an ergonomic intervention" for sexual dysfunction. Schrader et al. "Cutting Off the Nose to Save the Penis." J. Sex. Med. (2008): 5:1932-1940 (see also Lowe et al. "Effect of Bicycle Saddle Designs on the Pressure to the Perineum of the Bicyclist." Med. Sci. Sports Exerc. (2004) 36(6): 1055-62).

Substantial effort has been directed to the impact of seat geometry on various factors related to ED. Munarriz et al. calculated a crude mean pressure exerted by subjects on their perineum when straddling a saddle (weight/surface area) and concluded that seat geometry can have a significant impact on penile hemodynamics. "Only the Nose Knows . . . " J. Sex. Med. (2005) 2:612-619. Breda et al. measured partial pressure of penile transcutaneous oxygen "to investigate the differences of compression from two different saddles on the vascular structures of the perineum." "Development of a New Geometric Bicycle Saddle for the Maintenance of Genital-Perineal Vascular Perfusion." J. Sex. Med. (2005) 2:605-611. That study suggests specific seat geometry was effective in "limiting the compression on the pelvic floor." A National Institute for Occupational Safety and Health report ("No-nose Saddles for Preventing Genital Numbness and Sexual Dysfunction from Occupational Bicycling" NIOSH Pub. No. 2009-131) reports no-nose saddles are effective "in reducing pressure in the groin and improving the sexual health of male bicycle patrol police officers" and that no-nose saddles may also benefit women.

There is, however, a fundamental flaw in those studies with respect to an accurate measure of pressure exerted on the perineum. Each of those studies estimate or measure the pressure exerted by the bicycle rider on the bicycle seat. Although a force exerted by a user on a surface is matched by a corresponding force exerted by the surface on the user, relying on a measure of the force on the bicycle seat does not provide information about the force exerted by the seat on a specific region of the user, including the perineum region. In particular, studies that position the pressure sensor on the bicycle seat do not provide an accurate indication of the pressure exerted on the perineal region, and specifically on a perineal blood vessel. This is especially problematic as a bicycle rider is constantly moving with respect to the saddle so that a pressure on the seat cannot be reliably correlated with a specific region of the perineum. Instead, the pressure sensor on the bicycle seat measures pressure exerted by the rider onto the bicycle seat and, depending on how the rider is seated, non-perineal regions may exert significant pressure on the seat surface. Accordingly, there is a need in the art for systems that can reliably and accurately measure a force or a pressure on the perineum of a user positioned on a bicycle seat in order to precisely evaluate risk of ED by various bicycle seat geometries.

SUMMARY OF THE INVENTION

Provided herein are various devices and methods for measuring the pressure on the perineum of a user positioned on a surface. The methods and devices are further useful for evaluating the risk of erectile dysfunction (ED) for a user positioned on a surface, including evaluating that risk for different bicycle seat compositions and geometries, specifically for bicycle seats. The methods and devices presented herein provide distinct and significant advantages over other systems used to measure pressure. For example, devices disclosed herein directly measure the pressure exerted on the perineum region and, in particular, at multiple precise key locations corresponding to artery blood vessels of the perineum. Conventional devices, in contrast, have measured the pressure exerted by the rider on the surface seat and attempt to extrapolate those measurements to a force on the perineum. The fundamental flaw in those devices, however, is that those devices do not actually measure perineum pressure, and certainly not the pressure exerted on specific blood vessels of the perineum. Connecting sensors to the perineum in a geographically coherent manner addresses the concern that non-perineum regions, such as the sit bones, exert forces on the seat. In addition, certain regions of the perineum are more sensitive to external pressure than other regions, such as those perineum regions directly over a perineum blood vessel. Accordingly, the devices and methods disclosed herein relate to sensors that are affixed to the perineum region of the user, rather than to a surface on which the user is placed. Furthermore, the device is configured to be portable so that it can be used during real-time activity including active riding in an outdoor setting. Other devices, in contrast, are limited to stationary bicycles in that the sensors must be directly fed to a computer or display and/or are too large to be able to be carried by the user without adversely affecting the exercise and/or rider motion.

In an aspect, the user is a rider and the surface corresponds to a bicycle seat or saddle. The bicycle seat may be part of a regular bicycle such as a racing bike, road bike, mountain bike or a hybrid. Alternatively, the bicycle seat may be part of a stationary bicycle or a simulated bicycle that is used as part of a bicycle seat-testing apparatus. In this aspect, the user may be a human or may be a dummy or dummy portion anatomically modeled against the perineum region geometry and adjacent regions that are normally positioned on the seat. In an aspect, the user is a human male and the exercise is non-stationary bicycle ride wherein the device obtains a real-time measure of pressure on the perineum under normal ride conditions without adversely affecting user motion or the ride.

In an aspect, any of the methods and devices disclosed herein measure the pressure exerted by a surface on the perineum of a user supported by the surface. A pressure sensor or plurality of pressure sensors are connected to the perineum region of the user. The user is positioned on the surface, wherein the pressure sensor is positioned between the perineum and the surface. Output from the pressure sensor is obtained while the user is positioned on the surface. Optionally, the surface is formed from a bicycle seat and the method further relates to evaluating the risk of erectile dysfunction associated with the bicycle seat and the user from the obtained output.

In an embodiment, the invention is a method of evaluating the risk of erectile dysfunction associated with a user using a bicycle seat by connecting a pressure sensor to the perineum region of the user who will use the bicycle seat. The user is positioned on the bicycle seat. The output from the pressure sensor while the user is positioned on the bicycle seat is obtained. The obtained output is analyzed, thereby evaluating the risk of ED.

In an aspect a plurality of pressure sensors are connected to the perineum region of the user to obtain a pressure map of the perineum region. In this manner, more precise evaluation of the risk of erectile dysfunction is possible, as different seats may generate different magnitudes of pressure at different perineum regions. A pressure map is useful for more precisely defining risk regions having locally high pressure points corresponding to particularly sensitive regions in the perineum, such as corresponding to a blood vessel. Accordingly, an embodiment of the invention relates to a pressure map that corresponds to the pressure on one or more of the arteries of the perineum region selected from the group consisting of: left proximal artery; left distal artery; right proximal artery, right distal artery, and internal pudendal artery. In an aspect the pressure map is generated from two sensors, three sensors, four sensors, five sensors, six sensors, seven sensors, or eight sensors. In an aspect, the pressure map is generated by a plurality of sensors selected from a range that is greater than or equal to 2 and less than or equal to 8. In an aspect, four pressure sensors are used that provide a pressure map based on the pressure exerted on the left and right internal pudendal artery at a distal and proximal position. In an aspect, six pressure sensors provide a pressure map based on the pressure exerted on the left and right internal pudendal artery at a distal, mid and proximal position (wherein the mid position is between the proximal and distal positions). In an aspect, the sensors are pressure sensors, such as a pressure transducer whose voltage output is related to the force exerted on the force-sensing element such as a resistor whose resistance changes depending on the applied force.

In an embodiment, the sensor output is a time course of the pressure map. The length of time of the time course is limited only by the capacity of the memory storage of the microcontroller. Accordingly, as the desired period of measurement increases, hardware is corresponding selected to ensure that the data from the sensor outputs are reliably stored. In an aspect, the time course is for a period that is greater than or equal to two hours, or selected from a range that is greater than or equal to 30 minutes and less than or equal to 4 hours. Such a time length is beneficial as the user may have different positions as the ride proceeds due to fatigue.

In another aspect, the data acquisition frequency is adjusted to provide different time sensitivity. For example, in certain embodiments of the invention the use is non-stationary bicycle riding for a time period. That time period may be relatively long, such as for bicycle seats used in long-distance riding on the order of hours or more. In that situation, the data acquisition frequency may be lowered, thereby extending the time period of active data acquisition. Alternatively, for seats used in relatively short-term rides (or for short-term seat testing), the acquisition frequency may be increased to provide more frequent pressure measurement. In an aspect, the data acquisition frequency is about 20 Hz, between about 10 Hz and 30 Hz, or is selected based on the cadence of a rider, so that data acquisition occurs at least twice during the range of pedal motion. Under different ride conditions and users, cadence may range from 50 rpm to about 120 rpm. In an aspect, the acquisition may be periodically turned on and then turned off to ensure data is sampled over the entire ride.

In an embodiment, the invention further relates to an analyzing step that further comprises comparing the obtained output to a user-selected pressure level. In an aspect, the user-selected pressure level is related to the occlusion pressure for the corresponding blood vessel over which the sensor is placed. In an aspect, the user-selected pressure level is the occlusion pressure. In an aspect, the user-selected pressure level is a fraction of the occlusion pressure, such as greater than or equal to 80%, greater than or equal to 90%, or selected from a range that is greater than or equal to 80% and less than or equal to 100% of the occlusion pressure.

In an aspect, the risk of erectile dysfunction is identified as high for a bicycle seat that exerts a maximum pressure on the perineum that is greater than or equal to the user-selected pressure level for a time period that is greater than or equal to a user-selected time period. This aspect is recognition that risk can be related to not only the magnitude of the pressure on the perineum but also the duration. In addition, duration may be influenced by the seat and the bike geometry, with certain geometries resulting in longer duration of a user position fixed relative to the seat, and other geometries facilitating shifting position that may help alleviate perineum pressure. In an embodiment, the time period is an absolute magnitude, such as greater than 10 seconds, greater than 30 seconds, greater than 1 minute, or selected from a range that is greater than or equal to 1 second and less than or equal to 1 minute. In another aspect, the time period refers to a continuous span of time. Alternatively, the time period may be the sum of different time spans such as a user who, during a course of ride, reaches the user-selected pressure level a large number of times, but each individual time may be relatively short. In an aspect, the user-selected time period is expressed as a percentage of the sampled time, including a percentage of the total ride time for when the data acquisition is for the entire time period. Depending on the rider, seat geometry, ride characteristics or route, the percentage of time a measured pressure meets or exceeds occlusion pressure ranges from 0% to 50%. Accordingly, risk is optionally assessed in terms of such a percentage, such as a percentage of time that meets or exceeds occlusion pressure that is greater than about 1%, 5%, 10% or 20%, with risk factor assigned depending on desired stringency conditions (e.g., high for 5% or greater, medium for between 1% and 5% and low for less than 1%). The actual cut-off values for magnitude or risk are assigned depending on degree of risk tolerance in the particular setting.

Any of the methods and device disclosed herein optionally relate to a user-selected pressure level that corresponds to a perineal artery occlusion pressure.

In an aspect, the methods further relate to determining the perineal artery occlusion pressure for the user. There are various methods for determining occlusion pressure of a blood vessel, including perineal arteries. For example, occlusion pressure may be determined by observing blood flow in the vessel and identifying occlusion pressure as the point at which the applied pressure results in no blood flow through the vessel. Examples of techniques that measure blood flow in a blood vessel include Doppler ultrasound. Alternatively, indirect measures of blood flow may be used, including oxygen readout such as pulse oximetry. In one embodiment, the method for determining occlusion pressure on a perineal artery comprises exerting a pressure on a perineal artery of the user, identifying the pressure as the perineal artery occlusion pressure for the user; and identifying the output of the pressure sensor for the perineal artery occlusion pressure to obtain an occlusion pressure sensor value. This can be achieved by directly exerting a pressure on the pressure sensor that is over the perineal region and using a technique such as Doppler ultrasound to identify the sensor output value corresponding to stopped flow. Alternatively, the sensor may be separately calibrated, and a known pressure applied to the perineum region corresponding to an occlusion pressure without any sensor affixed thereto.

In an aspect, the analyzing step comprises comparing a maximum output of the pressure sensor against the occlusion pressure sensor value and identifying erectile dysfunction risk as high for a maximum output that is greater than or equal to the occlusion pressure sensor value.

In an aspect, any of the methods and devices disclosed herein is for measuring the pressure exerted by a surface on the perineum of a user supported by the surface. Optionally, the measured pressure, including pressure time course and pressure map time course, is used to evaluate the risk of erectile dysfunction associated with the user's use of the seat surface as a support. In an embodiment, the seat surface is the surface of a saddle, such as a bicycle saddle.

In another embodiment, provided herein is a method of assessing a bicycle seat erectile dysfunction risk factor for a user of the bicycle seat. A bicycle seat having a surface with a geometry is provided. A plurality of pressure sensors are connected to the perineum of the user to obtain a pressure map of the perineum. The pressure sensors may be strategically positioned to provide information about pressures exerted against the blood vessel of the perineum and/or at different locations of a perineal blood vessel. The user is introduced to the bicycle seat surface to at least simulate bicycle riding, wherein the pressure sensors are positioned between the perineum and the bicycle seat surface. In an aspect, the activity is bicycle riding. In an aspect, the activity is simulated bicycle riding, such as a bicycle seat mounted in a stationary configuration. In an aspect, the activity is riding of a stationary bike. Alternatively, the activity is non-stationary riding of a bike, including outdoor riding under real conditions (e.g., road, cross-country, mountain and/or a combination thereof). A time course of the perineum pressure map is obtained from the plurality of pressure sensors. The bicycle seat erectile dysfunction risk factor is assessed from the obtained time course.

There are various protocols for assessing ED risk factor for a bicycle seat, depending on desired stringency. One example of a highly stringent assessment is identifying a risk factor as low only for those seats that demonstrate a maximum pressure output that is always less than 80% of the occlusion pressure level. A medium stringent assessment is for the maximum exerted pressure is less than 90% of the occlusion pressure level. A low stringent assessment is for the maximum exerted pressure is less than the occlusion pressure level. These examples correspond to a bike seat being a high risk for being an independent factor of ED for maximum pressure output greater than 80% (high stringent criteria), greater than 90% (medium stringent criteria) or greater than or equal to 100% (low stringent criteria) of the occlusion pressure level.

In an embodiment, the assessing step relates to comparing a maximum pressure output from the time course and identifying the bicycle seat erectile dysfunction factor as at least medium for maximum pressure output that is greater than or equal to a user-selected pressure, such as a user-selected pressure that is equal to a perineum blood vessel occlusion pressure, or a fraction thereof such as between 80% and 100%.

In an embodiment, the assessing step optionally relates to the length of time the observed pressure exceeds the user-selected pressure. In an aspect, the bicycle seat erectile dysfunction factor is identified as high for maximum pressure output that exceeds the user-selected pressure for a user-selected time period. Depending on the desired stringency, the time period is accordingly selected. Conservative ED risk assessment will generally have a shorter user-selected time period (e.g., on the order of seconds) than less-conservative assessments (on the order of tens of seconds to minutes). The user-selected time period is optionally expressed as a percentage of the total ride or percentage of the total sampling time period, such as 1%, 2%, 5% or 10% or any desired range that reflects the desired stringency.

In an aspect, the method further relates to modifying the bicycle seat surface geometry to minimize the bicycle seat erectile dysfunction risk factor. In particular, bicycle seats having low ED risk factors may be at least partially empirically determined by obtaining perineum pressure maps for the various seats during bicycle riding. For example, a seat geometry or material construction (e.g., padding) may be modified or redesigned such that the maximum pressure output of the time course is reduced by at least 20%.

In another embodiment, the invention is a device, such as a device for implementing any one or more of the methods disclosed herein. In an aspect the device is for measuring perineal pressure during bicycle riding having a plurality of pressure sensors adapted for connection to a perineal region of a bicycle rider for generating a pressure map over the perineal region. The sensors are operably connected to a microcontroller that stores a time course of the pressure map from the plurality of pressure sensors, wherein the microcontroller is self-contained and functionally portable. The device, and related methods, can use any number of sensors as desired. There is, however, a generally practical upper-limit to the number of sensors required to accurately measure the map because there are certain relevant positions in the perineum region. These positions are over important blood vessels. Accordingly, as the number of sensors increase, redundant and unnecessary measurements will be obtained. Accordingly, in an aspect, the plurality number is less than or equal to 16, less than or equal to 8, or is 6 or 4 sensors. In an embodiment, the microcontroller is connected to the plurality of pressure sensors by a signal-conducting wire.

In an aspect, the pressure map comprises a pressure exerted against one or more of the arteries of the perineal region, the arteries selected from the left proximal artery, left distal artery, right proximal artery, right distal artery, and pudendal artery.

In an aspect the microcontroller is adapted to be positioned on the bicycle rider. In this manner, the microcontroller may be carried in the pocket of a piece of clothing the rider wears, may be secured around a limb, or may be placed within a pack that is carried by the user.

Although specific exemplifications herein relate to a bicycle riding setting, the devices and methods provided herein are useful in a number of fields including in industrial design to maximize comfort for a user supported by a surface for an extended period of time (e.g., seats, chairs, benches, swings, horse saddles, motorcycle seats, pilot seats, airplane seats, automobile seats).

DETAILED DESCRIPTION OF THE INVENTION

Figure 1:
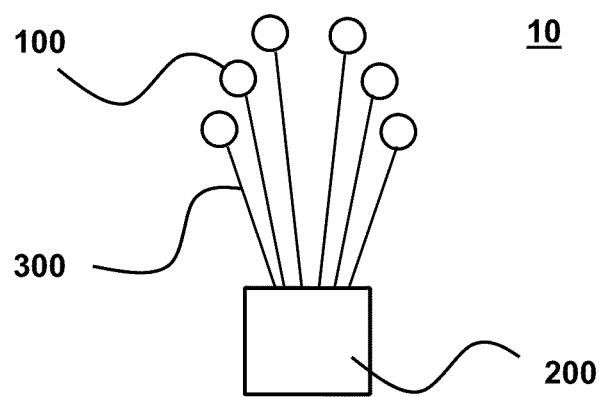
FIG. 1 is a schematic illustration of a portable device for measuring perineal pressure during riding, including bicycle riding.

"Surface" refers to an object's surface that supports a user that is positioned in a manner such that at least a portion of the user is supported. In particular aspects, the support is at least partially by the perineum region of the user. "Seat" refers to saddles, including a bicycle saddle connected to a bicycle or a simulated bike such as a stationary or exercise bicycle or a post for testing bicycle seats.

"Perineum region" refers to an area between the pubic symphysis and the coccyx and is used to refer to both the surface region and underlying structure such as blood vessels, including blood vessels that supply blood to the penis in males. In particular, it is that region that is generally supported by a conventional bicycle seat.

"Output" refers to a signal that is generated by a sensor connected to the perineum region. Generally, the signal is an output voltage from a pressure or force sensor, whose voltage magnitude is dependent on the force applied to the sensor. "Connected" refers to a sensor that is reliably positioned in a specific location in the perineum region. A sensor connected to the perineum region of the user is fundamentally different than a sensor connected to a seat surface. Sensors connected to the seat surface do not measure the pressure exerted on the perineum, but instead measure the total pressure exerted by the user on the seat surface, which may have non-perineum generated forces, such as sit bones or other regions of the user adjacent to the perineum. The sensors are secured to specific regions of interest in the perineum, including directly above blood vessels of interest. Any means of connecting the sensor to the user may be used, including by underlying adhesives and/or overlying tape, dressing or bandage that facilitates temporary affixation. In an embodiment, a Tegaderm™ dressing may be used to reliably position and affix the sensor. Medical tape may also be used. So long as the affixation provides reliable positioning in that the sensors do not migrate during use and are not excessively padded (thereby causing an under-recording by the pressure sensor), any kind of affixation material may be used.

"Risk of erectile dysfunction" refers to assessing the pressure points generated by a bike seat on a male user and, for seats that generate pressures identified as relatively high identifying that seat as being an independent risk factor ED. The term risk is employed herein as it is understood that simply using a bike seat once for a short time period may not result in ED. However, continued, prolonged, and frequent use of bike seats that generate significant pressures on a perineum blood vessel will generate a significant independent risk of erectile dysfunction that depends, at least in part, on rider characteristics and positioning on the seat (e.g., amount of time spent "out of the saddle"). Nevertheless, all other factors being equal, a seat whose risk of erectile dysfunction is high means that a user is more likely to encounter ED-related issues than if the user used a seat having a lower risk of ED. Risk is characterized in terms of the output of the pressure sensor, including maximum output, with higher outputs being of higher risk. The assessment encompasses other useful algorithms including time-averaging, magnitude-averaging, and statistical processes related to peak values and fractions of time spent at or near a user-selected pressure. Similarly, "risk factor" refers whether a bike seat is more likely or less likely to be a significant independent contributing factor for ED. Furthermore, a variety of physical symptoms after a ride may be used to further define risk, including genital numbness and/or transient or short-term voiding. Those physical symptoms are commonly associated with a risk of ED.

"Pressure map" refers to the use of two or more sensors to provide a measure of pressure in the perineum region at distinct locations simultaneously. The pressure map is useful as certain seats or riders may specifically impinge very localized perineum regions that may otherwise be missed with a single sensor or pressure calculation. Furthermore, for seat design, it is important to understand how seat geometry impacts different locations of the perineum region.

"Time course" is used to refer to the fact that the pressure on the perineum may change over time. For example, a single point in time snap-shot of pressure on the perineum does not account for the fact that during a ride the pressures change as the rider shifts weight from one foot to the other, comes out of the saddle, rides up-hill, down-hill or on a level surface, or becomes fatigued. "Period" refers to the length of time the perineum pressure(s) are monitored or recorded. In one aspect, it is for the entire bike ride. In another aspect it is for a portion of the bike ride.

"Perineal artery occlusion pressure" refers to the pressure at which blood flow in the artery stops.

"Introducing" refers to a user that uses a bicycle seat. "Simulate bicycle riding" refers to a context where the bike seat may be undergoing testing so that, for ease of testing, the seat is connected to a stationary bicycle or even simply a post optionally having pedals to support the user's feet.

"Self-contained" refers to a microcontroller (and associated components such as power supply, pressure sensors, wiring) capable of being used in the field, such as during a bicycle ride outdoors. In contrast, a microcontroller that is not self-contained is not portable for real-time use but remains in the testing facility where it is hooked into a computer or other data-recording/observing device. Accordingly, the devices provided herein are said to be "functionally portable" in that they provide full use while in use with a bicycle ride, including an outdoor non-stationary ride situation, without adversely affecting the user's ride experience.

"Operably connected" refers to a configuration of elements such as device components, wherein an action or reaction of one element affects another element, but in a manner that preserves each element's functionality. Operably connected device components may be in contact, such as in electrical contact by a signal-conducting wire between a sensor and a microcontroller containing a microprocessor. Alternatively, operably connected components may be connected by one or more intervening components. In another alternative, operably connected components may not be physically connected, but may be wirelessly connected such that a signal is output from one component and wirelessly received by a second component.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

Example 1

Device Configuration

An important aspect of the perineal pressure measurement device is that it is self-contained. As a result, the device can be removed from a controlled setting and actually reliably used during the physical activity, such as bicycle riding. A drawback of many conventional measurement devices is that they are not self-contained, but must be hooked into a computer to analyze output from the sensor. Accordingly, provided herein is a portable device having a plurality of pressure sensors and a drive circuit to accommodate one or more sensors, wherein the device is completely self-contained. In an aspect, the device may accommodate up to eight sensors. A microcontroller receives analog inputs from the sensors and converts them to digital signals. The digital signals are stored and the data retrieved from the microcontroller, such as by a File Transfer Protocol (FTP) server.

Referring to FIG. 1, provided herein is a device 10 formed from a plurality of pressure sensors 100 and a microcontroller 200 that is self-contained and sufficiently small to be portable and carried, for example, on the body of a user. The pressure sensors 100 are operably connected to the microcontroller. FIG. 1 illustrates an embodiment where the connection is via signal-conducting wires 300, such as a wire that transmits a voltage output from the pressure sensor 100 to the microcontroller 200. Another example of an operable connection is via a wireless connection between sensor 100 and microcontroller 200.

Figure 2:
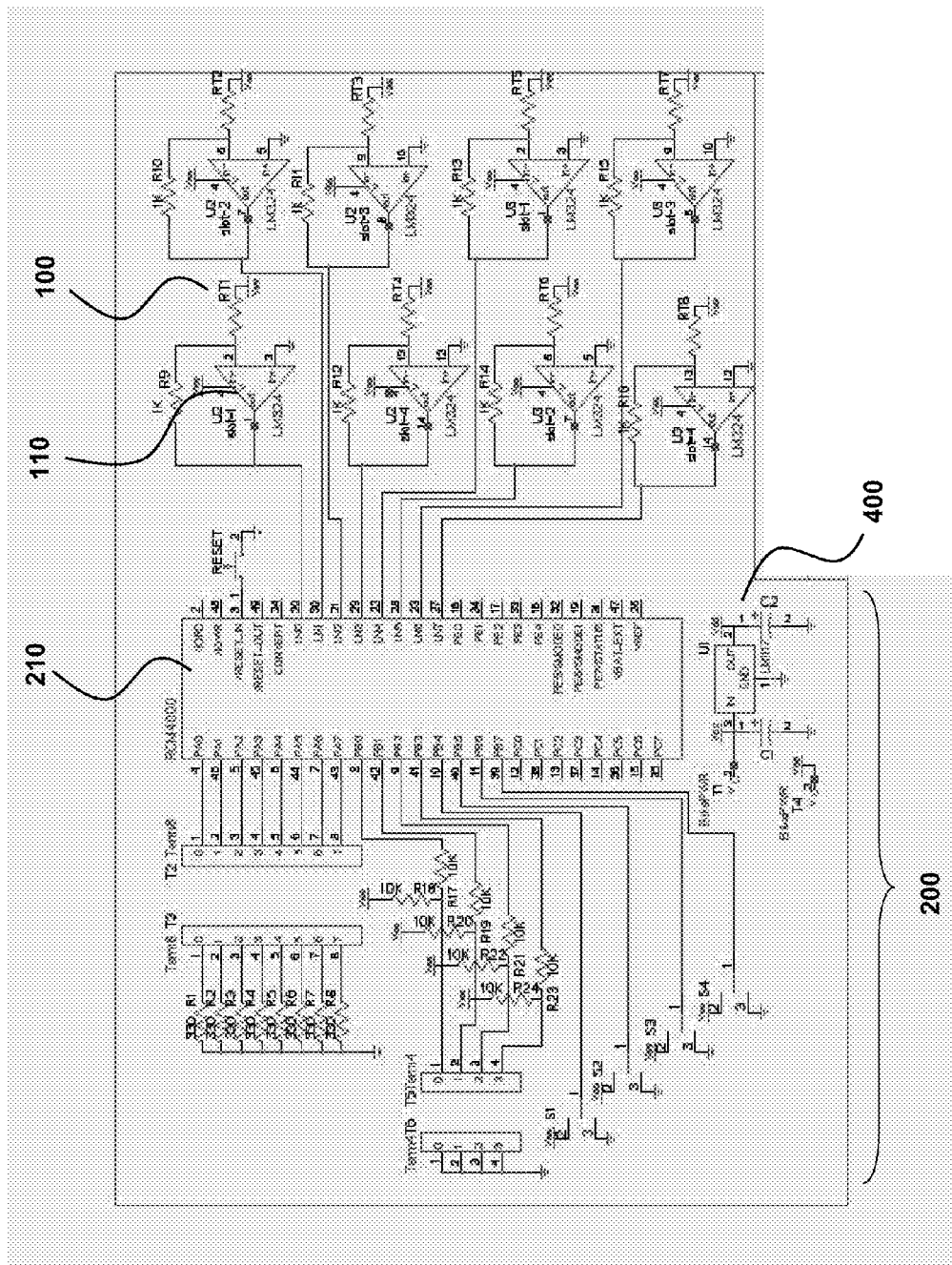
FIG. 2 is an electrical circuit for one embodiment of a portable perineal pressure monitor.

The microcontroller 200 contains a chip with memory storage capability for storing a time-course output from pressure sensors 100. Alternatively, the microcontroller may transmit the output to a remote location where the data is stored, observed, and/or analyzed. In an embodiment, the microcontroller chip is an RCM4000 RabbitCore® microprocessor (see, e.g., www.rabbit.com/products/rcm/4000/) that receives analog input from the sensors and converts them into digital signals to be stored in its memory. FIG. 2 is an electrical circuit diagram of one embodiment of the device. The sensors 100 are electrically connected to a microprocessor 210 confined in microcontroller 200 portion such as via individual operational amplifiers 110. Other optional components are included in the microcontroller as desired, including switches and LED to indicate sensor and/or recording status. In this example the operational amplifiers are National Semiconductor LM324 low power quad operational amplifiers. The device may be powered by a power source 400, such as a battery for portable use or connected to a stationary source of power such as for seat testing under controlled conditions (e.g., in a laboratory setting with a stationary or other simulated bicycle). To enhance portability, the eight individual op-amps can be replaced with two low power quad op-amps. This has an advantage of decreasing the power requirements, dimensions, and the weight of the device.

Figure 3:
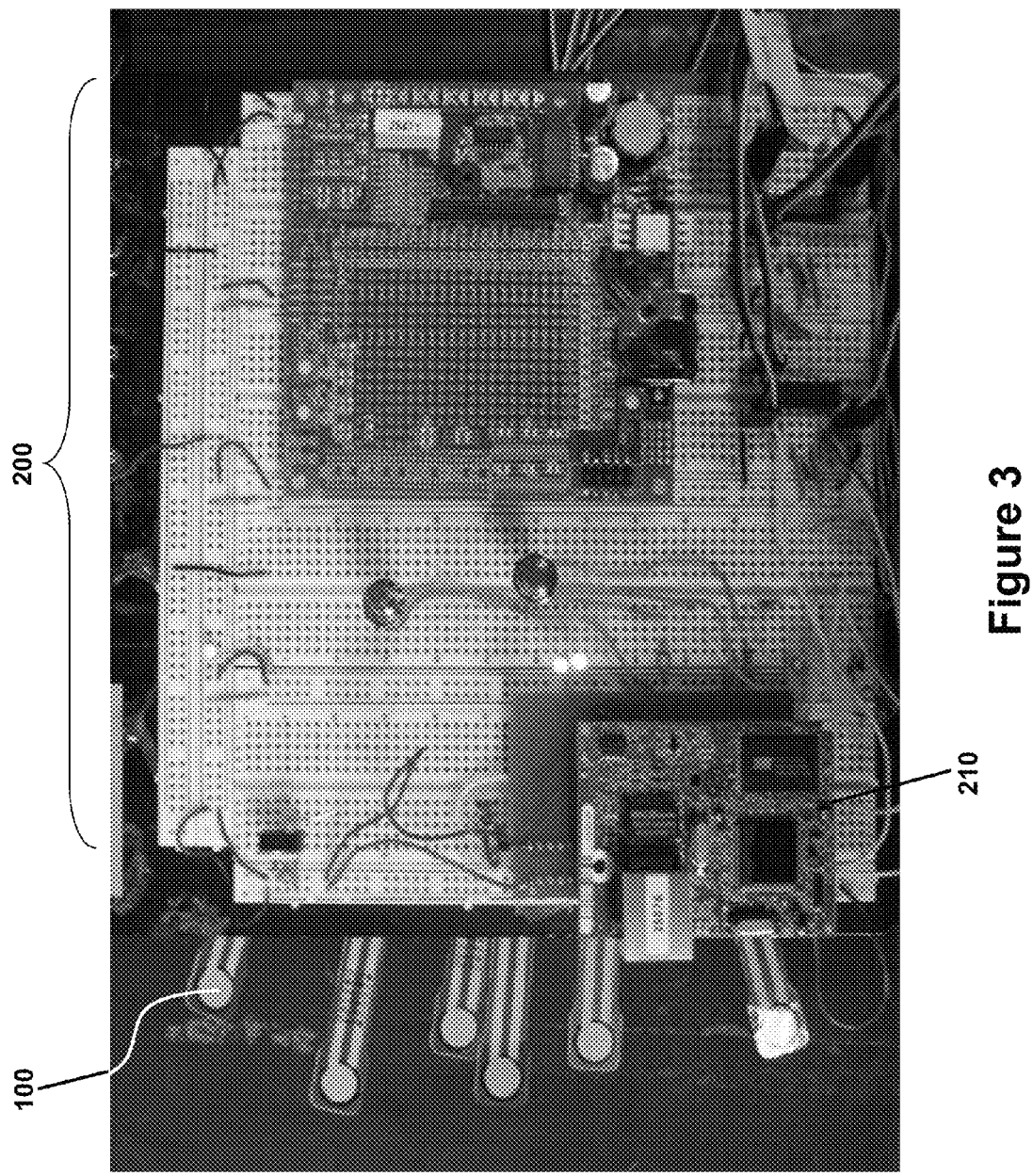
FIG. 3 is a photograph of one embodiment of a portable perineal pressure monitor.

FIG. 3 is a photograph of a device. The RCM4000 microprocessor 210 is embedded in a motherboard and a plurality of sensors 100, are operably connected thereto, such as via electrical connections to the motherboard to which the microprocessor is connected. Any sensor known in the art may be used so long as the sensor is capable of reliably providing a time course of force or pressure during the bicycle exercise. For example, the sensor may be a transducer, including a pressure or a force transducer. As used herein, force transducer and pressure transducer are used interchangeably as the measure of one parameter may be used to calculate the other parameter by the formula $P=F/A$, where P is pressure, F is force, and A is the area over which the force is applied. One example of a suitable sensor is a Flexiforce® force sensor from Tekscan (South Boston, Mass.) (see, e.g., U.S. Pat. No. 6,272,936). Any sensor, however, that is thin so as to provide non-intrusive measurement and capable of reliable positioning to a confined region within the perineum region of a rider may be used. In an aspect, the sensor measures the force over an area that is circular having a diameter that is less than or equal to 1 cm, 0.8 cm, 0.5 cm or about 0.95 cm (0.375").

The sensor may be incorporated into a force-to-voltage circuit as shown in FIGS. 2 and 3. The device shown in FIG. 3 has a final dimension of 9×9×4.5 cm with a total mass of 200 grams and, with the components exemplified therein, pressures from six distinct perineal locations can be stored for up to four hours. The portability of the device allows placement of the microcontroller portion on the rider's person, such as in a pocket or pack, without interfering with the cycling experience.

Example 2

Use of the Device

Figure 4:
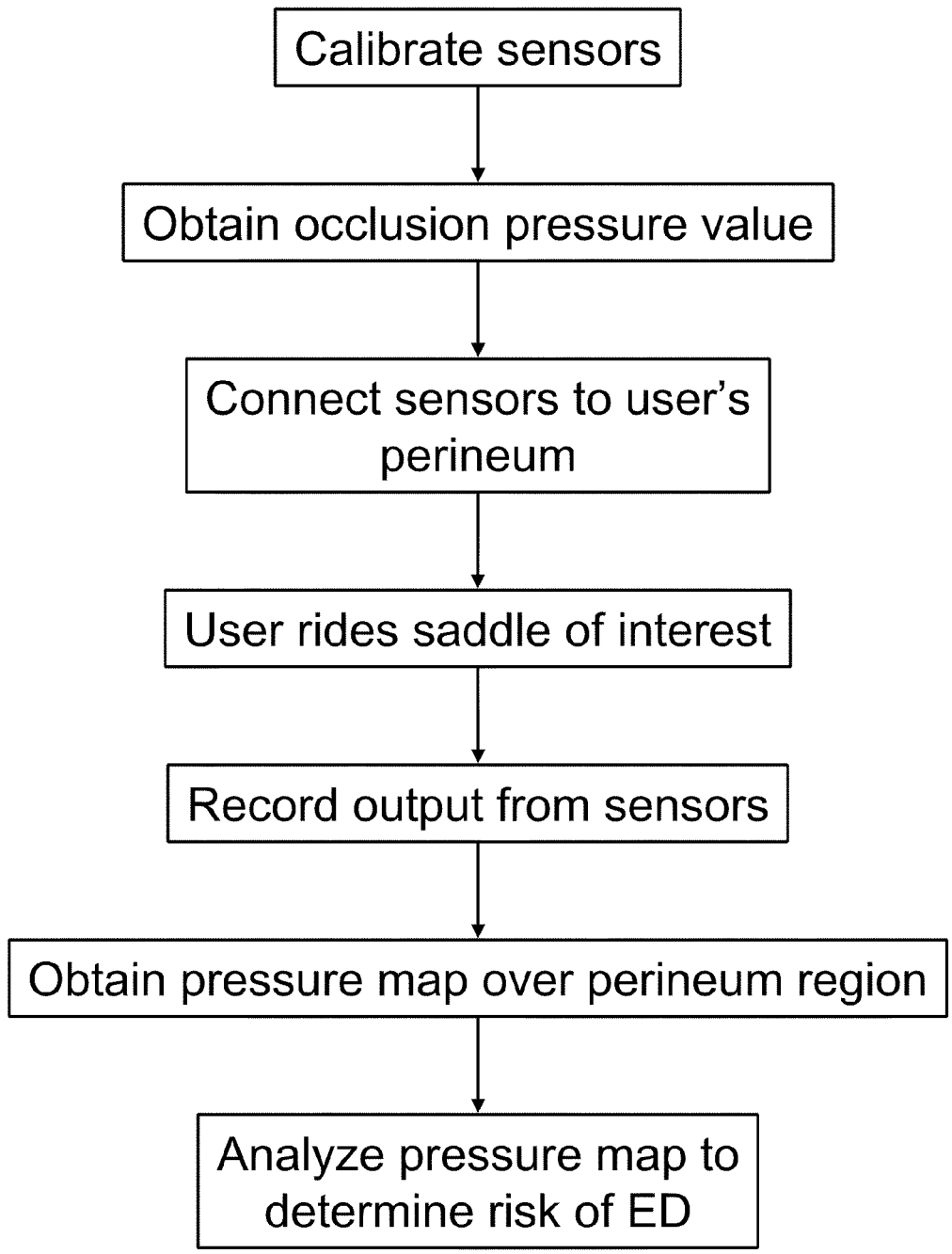
FIG. 4 is a flow-diagram of a methodology to evaluate the risk erectile dysfunction with a user using a seat, such as a bicycle rider positioned on a bicycle seat.

FIG. 4 summarizes various aspects related to use of the device to assess risk of erectile dysfunction. As a preliminary step, the sensor is calibrated so that an output from the sensor corresponds to a force or pressure, as desired. There are many types of calibration procedures for generating a calibration curve so that a pressure may be calculated for a given sensor output, such as voltage. For example, a sensor may be connected (e.g., taped) to the center of a syringe plunger orifice. A force is applied by placing a known weight directly to the top of the syringe stopper. Because both the orifice cross-sectional area and the applied force (from the weight) are known variables, the pressure exerted on the sensor is known. The voltage output from the sensor is obtained, such as a mean of several separate measurements, for a given applied pressure. The pressure is varied by applying different weights so that a pressure versus output voltage calibration curve is obtained.

To assist in the risk of ED analysis, the occlusion pressure value is optionally determined for the specific user in order to inform selection of the "user-selected pressure" in the ED risk assessment step. Alternatively, tabulated values of occlusion pressure may be consulted and extrapolated to the user (e.g., based on one or more of body size, weight, geometry, age). There are various methods by which the pressure at which an artery occludes may be determined. In one aspect, the method is by Doppler ultrasound measurement of peak systolic velocity (PSV) of a blood vessel, such as cavernosal artery PSV, wherein various pressures are exerted onto the perineum and against the blood vessel wall. The pressure may be reliably exerted by using a syringe having a transducer placed in the center of the syringe stopper, wherein the syringe is applied to the desired perineum region and PSV measured downstream from the pressure application region. For example, the artery at the bifurcation of the bulbar and cavernosal arteries is located. Peak systolic velocity (PSV) readings are obtained via Doppler ultrasound without any pressure on the perineum. The transducer is then positioned 2 cm superior to the ischial tuberosity and adjacent to the ischiopubic bone. A gentle steady pressure is applied perpendicular to the perineum until PSV is lost, as measured by the ultrasound probe transducer. The pressure is then gently released until flow is determined to have returned. This procedure is repeated multiple times, such as five times. The entire procedure is then repeated for the contralateral side. These steps are repeated for different perineum artery positions, as desired such as at about 4 cm from the tuberosity and at the bifurcation of the artery. In this manner, perineum blood vessel occlusion pressure is determined for different perineum positions. In an aspect, the bicycle ride is performed on a separate day to allow time for the user to rest.

Before the ride, the pressure sensors may be placed at the same locations where the occlusion pressure forces were applied, such as at specific locations along the internal pudendal artery. In this manner, a time course of pressure on the perineum is obtained, and if multiple sensors are used, a time course pressure map of the perineum region. The time course can be compared against occlusion pressure to provide an indication of ED risk.

Example 3

Representative Data

Figure 5:
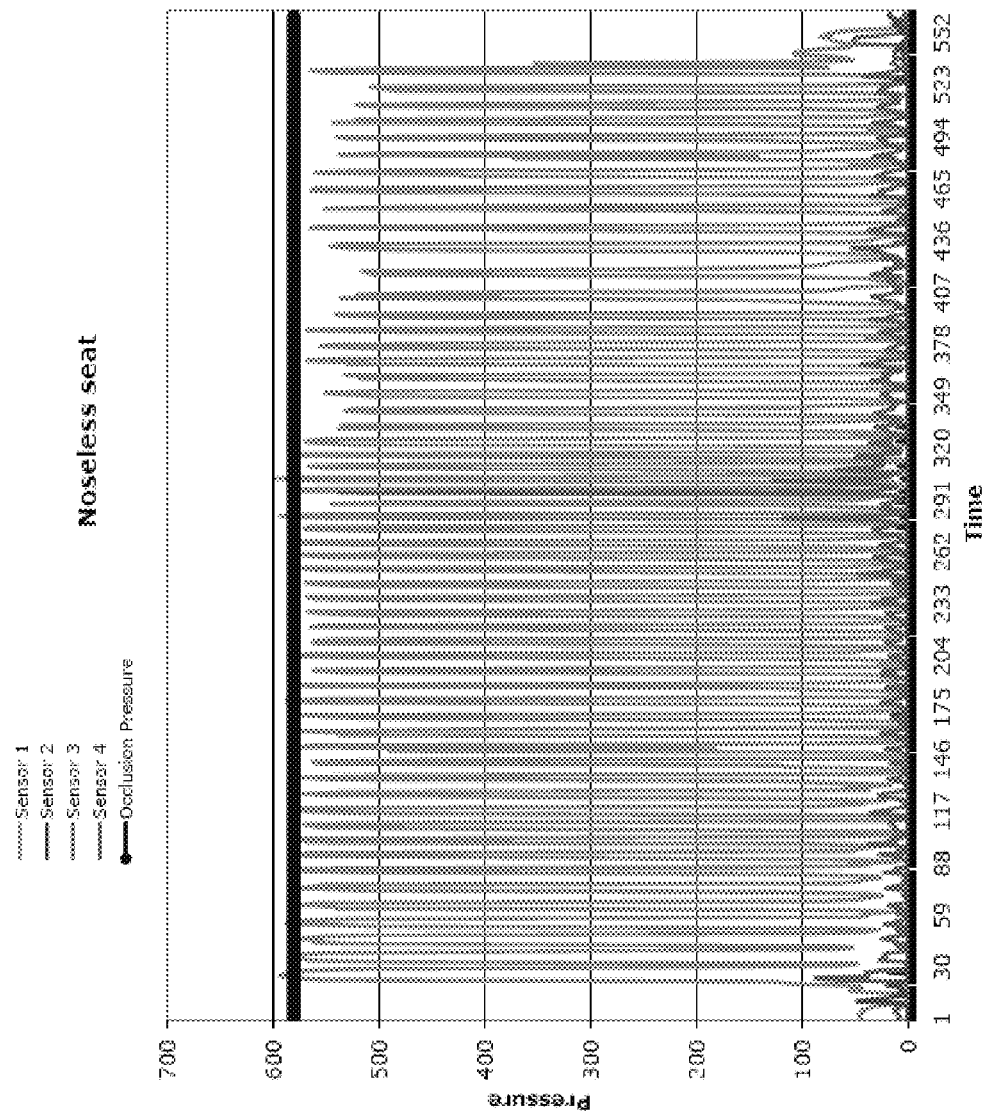
FIG. 5 is a time course of pressure obtained from four individual pressure sensors during a portion of a bicycle ride on a noseless seat. The occlusion pressure is indicated by the horizontal line.
Figure 6:
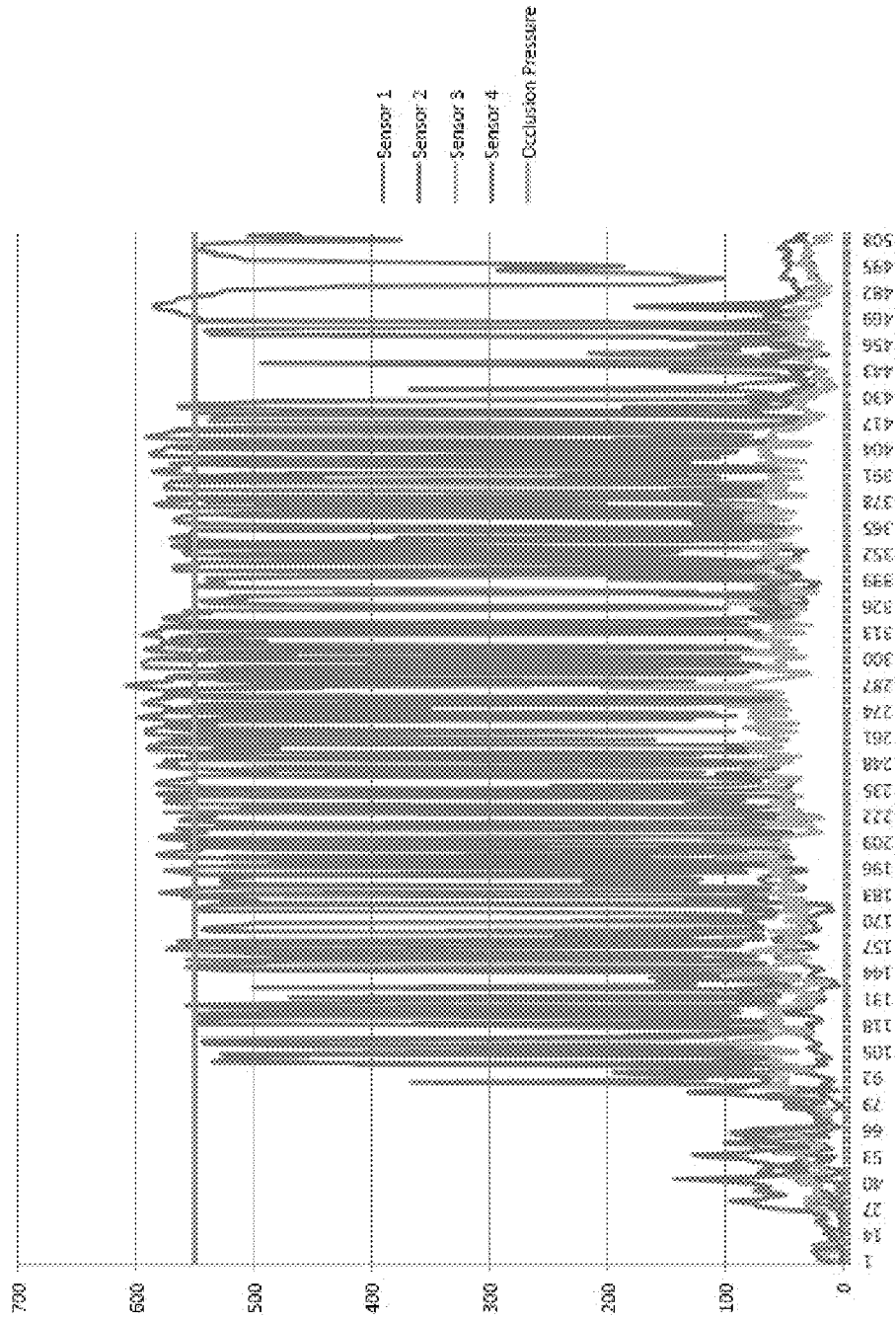
FIG. 6 is a graph of the output from various pressure sensors during a portion of a bicycle ride on a padded seat.

FIGS. 5-6 are representative results for a noseless and padded saddle, respectively, during a bicycle ride. In this example, the voltage output from four different sensors are plotted along with the voltage corresponding to the occlusion pressure value. The sensors are positioned over various perineum blood vessels, in this example four sensors over the left and right internal pudendal artery in a distal and proximal location. The results indicate that even noseless seats (FIG. 5), reported to relieve perineum pressure, actually in fact can generate sufficient forces on certain regions of the perineum to risk blood-flow stoppage. Temporary lack of blood flow in the perineum has been associated with ED and so can be a significant risk factor for ED. Similar results are obtained for a user cycling on a padded seat (FIG. 6). These results are surprising, as previous studies that apply sensors to the saddle (rather than the perineum), suggest opposite results. These data support the finding that the methods and devices disclosed herein are suitable for measuring perineum pressures exerted by a surface and for use in design or user selection of bicycle seats to increase comfort and/or reduce risk of sexual dysfunction, including ED. The output is plotted in terms of voltage output from the sensor, but is readily converted to a pressure if desired from a calibration curve. Accordingly, output may be a direct output from the sensor such as voltage, or alternatively may be processed and expressed in a different form, such as force or pressure, as desired.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a sensor number, volume or size range, temperature range, a length range, a time range, a velocity, a pressure or rates thereof, a composition, or a concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A method of measuring the percentage of the arterial occlusion pressure exerted by a surface on one or more arteries of the perineum of a human male user positioned on the surface, said method comprising the steps of:
   connecting a pressure sensor to the perineum region of the human male user, wherein the pressure sensor is not affixed to the surface;
   positioning the human male user on the surface, wherein the pressure sensor is positioned between one or more arteries of the perineum and the surface;
   obtaining output from the pressure sensor while the human male user is positioned on the surface;
   comparing the output to the arterial occlusion pressure of the one or more arteries of the perineum; and
   determining the output's percentage of the arterial occlusion pressure.

2. The method of claim 1, wherein the surface is formed from a bicycle seat and the method further comprises the step of:
   evaluating the risk of erectile dysfunction by the bicycle seat on the user from the obtained output.

3. The method of claim 2, wherein a plurality of pressure sensors are connected to the perineum region of the user to obtain a pressure map of the perineum region.

4. The method of claim 3, wherein the pressure map corresponds to the pressure of one or more of the following arteries of the perineum region selected from the group consisting of: left proximal artery; left distal artery; right proximal artery, right distal artery, and internal pudendal artery.

5. The method of claim 3, wherein the pressure map is generated by six individual pressure sensors.

6. The method of claim 3, wherein the output is a time course of the pressure map.

7. The method of claim 6, wherein the time course is for a period that is greater than or equal to two hours.

8. The method of claim 2, wherein the obtained output is from non-stationary bicycle riding for a time period.

9. The method of claim 2, wherein the evaluation step further comprises comparing the obtained output to a user-selected pressure level.

10. The method of claim 9, wherein the risk of erectile dysfunction is identified as high for a bicycle seat that exerts a maximum pressure on the perineum that is greater than or equal to the user-selected pressure level for a time period that is greater than or equal to a user-selected time period, wherein the user-selected pressure level is related to a perineal artery occlusion pressure.

11. The method of claim 10, further comprising the step of determining perineal artery occlusion pressure for the user by:
   exerting a pressure on a perineal artery of the user;
   identifying the pressure as the perineal artery occlusion pressure for the user; and
   identifying the output of the pressure sensor for the perineal artery occlusion pressure to obtain an occlusion pressure sensor value.

12. The method of claim 11 wherein the evaluating step comprises
   comparing a maximum output of the pressure sensor against the occlusion pressure sensor value; and
   identifying the risk of erectile dysfunction as high for a maximum output that is greater than or equal to the occlusion pressure sensor value.

13. A method of assessing a bicycle seat erectile dysfunction risk factor for a user of the bicycle seat, said method comprising the steps of:
   providing a bicycle seat having a surface with a geometry;
   connecting a plurality of pressure sensors to the perineum of the user to obtain a pressure map of the perineum, wherein the pressure sensor is not affixed to the surface;
   introducing the user to the bicycle seat surface to at least simulate bicycle riding, wherein the pressure sensors are positioned between the perineum and the bicycle seat surface;
   obtaining a time course of the perineum pressure map from the plurality of pressure sensors; and
   assessing the bicycle seat erectile dysfunction risk factor from the obtained time course.

14. The method of claim 13, wherein the assessing step comprises comparing a maximum pressure output from the time course to a user-selected pressure and identifying the bicycle seat erectile dysfunction factor as at least medium for maximum pressure output that is greater than or equal to a user-selected pressure.

15. The method of claim 14, further comprising identifying the bicycle seat erectile dysfunction factor as high for maximum pressure output that exceeds the user-selected pressure for a user-selected time period.

16. The method of claim 13, further comprising:
modifying the bicycle seat surface geometry to minimize the bicycle seat erectile dysfunction risk factor.

17. The method of claim 16, wherein the modification step reduces a maximum pressure output of the time course by at least 20%.

18. A device for measuring perineal pressure during bicycle riding, said device comprising:
a plurality of pressure sensors adapted for connection to a perineal region of a bicycle rider for generating a pressure map over the perineal region, wherein the plurality of pressure sensors are connected to the perineum region of the bicycle rider; and a microcontroller operably connected to the plurality of pressure sensors to store a time course of the pressure map from the plurality of pressure sensors, wherein the microcontroller is self-contained and functionally portable.

19. The device of claim 18, wherein the pressure map comprises a pressure exerted against one or more of the arteries of the perineal region, the arteries selected from the group consisting of:

left proximal artery;

left distal artery;

right proximal artery;

right distal artery; and pudendal artery.

20. The device of claim 18, wherein the microcontroller is adapted to be positioned on the bicycle rider.

* * * * *